United States Patent [19]
Nicoletti et al.

[11] Patent Number: 5,279,588
[45] Date of Patent: Jan. 18, 1994

[54] DEVICE FOR PROTECTING AGAINST ACCIDENTAL BUTTERFLY NEEDLE PUNCTURES

[76] Inventors: Pio Nicoletti, Via Caseificio 2; Renzo Cavallon, Localitá Ca' da Ronc, both of 38049 Vigolo Vattaro (Provincia di Trento), Italy

[21] Appl. No.: 828,280
[22] Filed: Jan. 30, 1992
[30] Foreign Application Priority Data Aug. 26, 1991 [IT] Italy .................. TN91U 000010

[51] Int. Cl.⁵ ............................................ A61M 5/00
[52] U.S. Cl. ................................ 604/250; 604/263
[58] Field of Search ............ 604/110, 164, 177, 192, 604/198, 250, 263, 174, 246, 167, 169

[56] References Cited

U.S. PATENT DOCUMENTS

| | | | |
|---|---|---|---|
| 2,941,778 | 6/1960 | Bujan | 604/250 X |
| 3,171,184 | 3/1965 | Posse | 24/248 |
| 3,595,230 | 7/1971 | Suyeoka et al. | 604/164 |
| 4,097,020 | 6/1978 | Sussman | 251/10 |
| 4,098,438 | 7/1978 | Taylor | 222/529 |
| 4,888,001 | 12/1989 | Schoenberg | 604/162 |
| 4,917,669 | 4/1990 | Bonaldo | 604/164 |
| 4,960,259 | 10/1990 | Sunnanväder et al. | 251/7 |
| 5,030,212 | 7/1991 | Rose | 604/263 |
| 5,084,032 | 1/1992 | Kornberg et al. | 604/263 |
| 5,108,376 | 4/1992 | Bonaldo | 604/171 |
| 5,112,311 | 5/1992 | Utterberg et al. | 604/177 |
| 5,120,320 | 6/1992 | Fayngold | 604/177 |
| 5,154,699 | 10/1992 | Ryan | 604/116 |
| 5,171,231 | 12/1992 | Heiliger | 604/263 |

FOREIGN PATENT DOCUMENTS

| | | | |
|---|---|---|---|
| 521563 | 10/1979 | Australia | A22B 5/14 |
| 0340427 | 11/1898 | European Pat. Off. | A61M 37/00 |
| 0459953 | 12/1991 | European Pat. Off. | |
| 0499077 | 8/1992 | European Pat. Off. | |
| 2845643 | 4/1980 | Fed. Rep. of Germany | 604/169 |
| 8804587 | 8/1988 | Fed. Rep. of Germany | A61M 1/14 |
| 2492261 | 4/1982 | France | A61M 5/14 |
| 9003196 | 4/1990 | PCT Int'l Appl. | |
| 9109638 | 7/1991 | PCT Int'l Appl. | |

Primary Examiner—C. Fred Rosenbaum
Assistant Examiner—Adam J. Cermak
Attorney, Agent, or Firm—Guido Modiano; Albert Josif

[57] ABSTRACT

The device for protecting against accidental butterfly needle punctures has a hollow body which delimits an internal accommodation seat for a butterfly needle which is connected to a flexible duct for feeding or withdrawing fluid. The seat has a proximal terminal portion, provided with two longitudinal lateral slits in each of which a respective wing of a butterfly needle can slidingly engage. The seat also has a distal terminal portion provided with retention members for engaging a butterfly needle. A butterfly needle can slide along the seat from a removal start position in the proximal terminal portion toward an irreversible complete retraction position within the distal terminal portion.

25 Claims, 3 Drawing Sheets

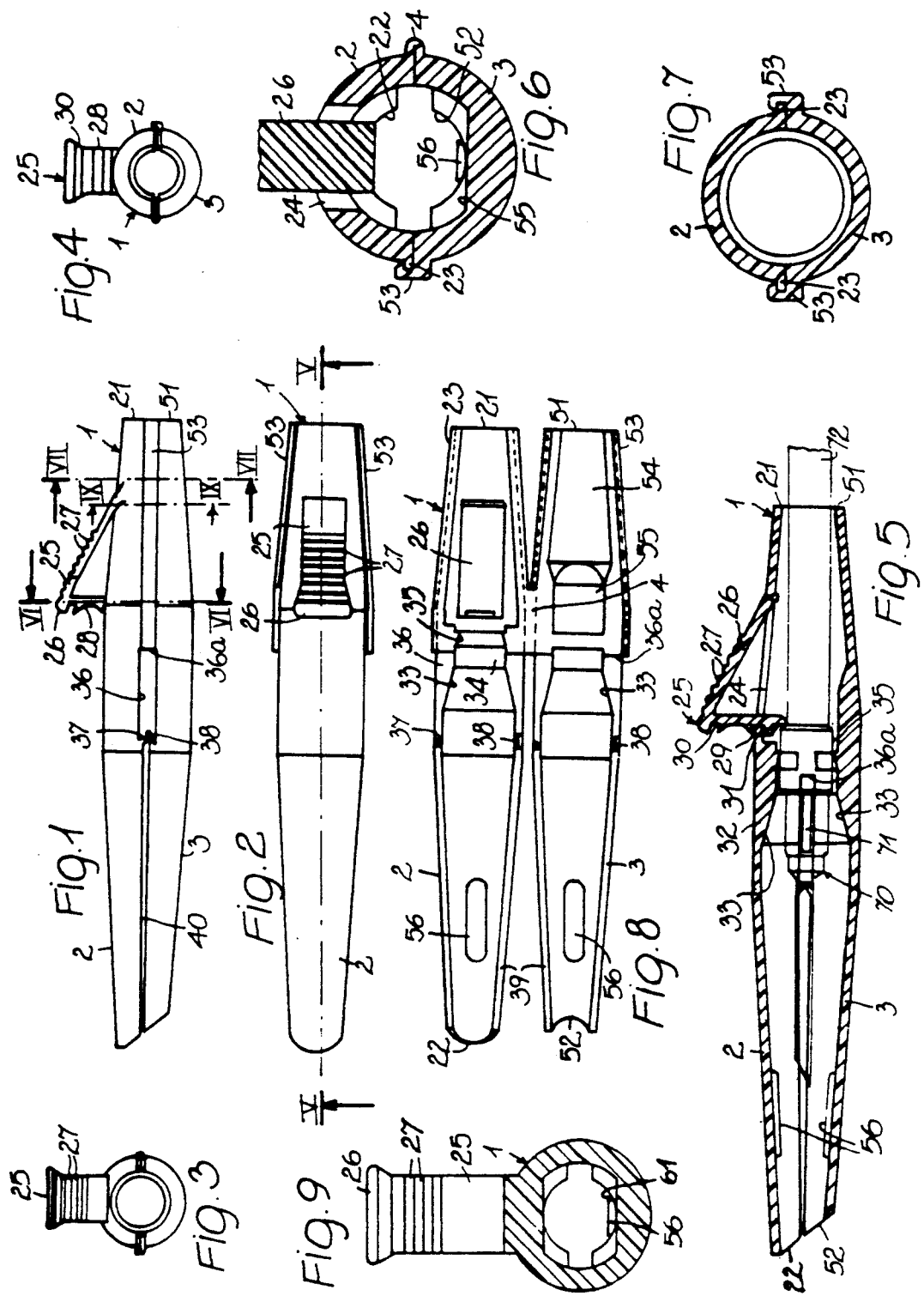

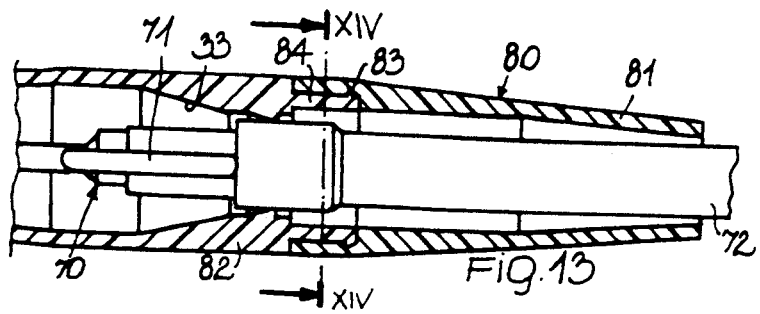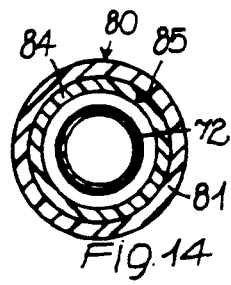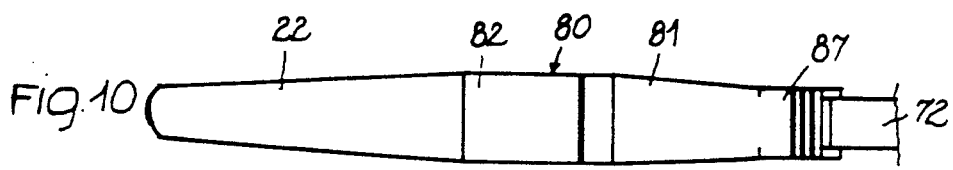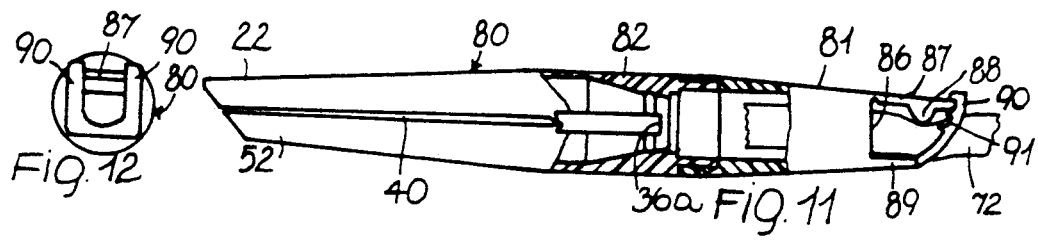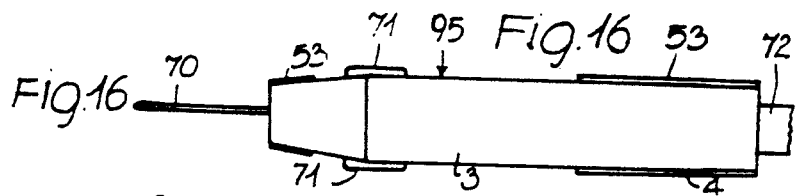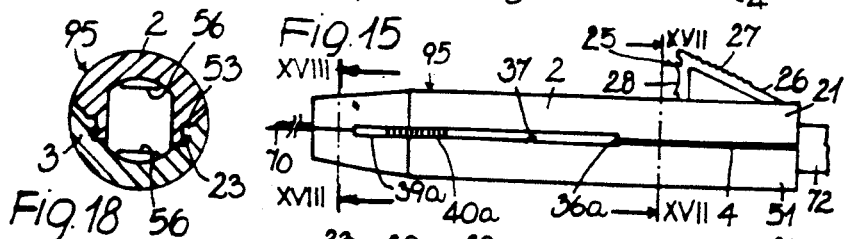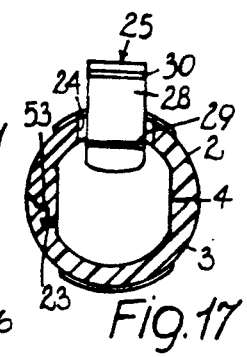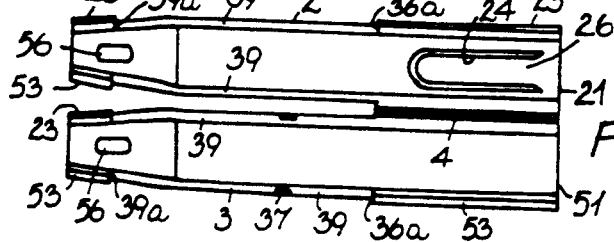

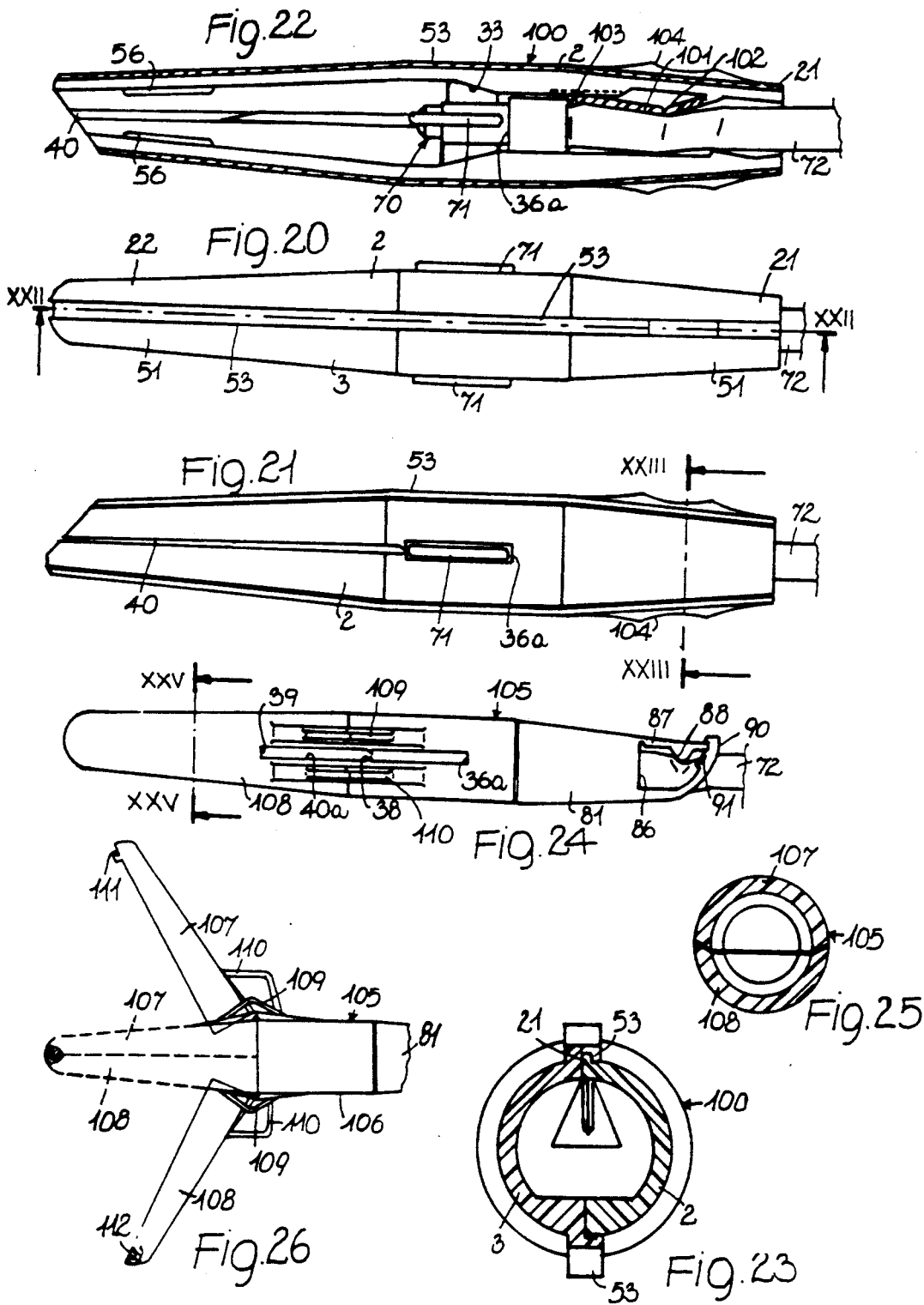

DEVICE FOR PROTECTING AGAINST ACCIDENTAL BUTTERFLY NEEDLE PUNCTURES

BACKGROUND OF THE INVENTION

The present invention relates to a device for protecting against accidental punctures caused by butterfly needles for phleboclysis, hemodialytic treatments, venous catheterizations and the like.

It is known that sanitary personnel assigned to hemodialytic treatment is exposed to the severe risk of being accidentally punctured by butterfly needles during and after removal thereof from the vein or arteriovenous fistula of a patient. If the needle is contaminated by infected blood, the operator can in fact be infected even in severe and irreversible form.

SUMMARY OF THE INVENTION

The aim of the present invention is to obviate this problem by providing a medical implement which can eliminate or drastically reduce the above mentioned risk factors.

An object of the present invention is to provide a protection device which is easy to use, highly safe and has a modest production cost.

This aim, this object and others which will become apparent hereinafter are achieved by a device for protecting against accidental butterfly needle punctures comprising a hollow body which delimits an internal accommodation seat for a butterfly needle connected to a flexible duct for feeding or withdrawing fluid, said seat having a proximal terminal portion, provided with two longitudinal lateral slits in each of which a respective wing of the butterfly needle can slidingly engage, and a distal terminal portion provided with retention means for the engagement of the butterfly needle, so that said butterfly needle can slide along said seat from a removal start position in the proximal terminal portion toward an irreversible complete retraction position within the distal terminal portion.

Advantageously, closure means suitable for engaging and choking the flexible duct in order to prevent the escape of residual fluid or blood from the needle are provided upstream of the distal terminal portion of said accommodation seat.

BRIEF DESCRIPTION OF THE DRAWINGS

Further aspects and advantages of the device according to the present invention will become apparent from the following detailed description of some preferred but not exclusive embodiments thereof, given only by way of non-limitative example with reference to the accompanying drawings, wherein:

FIG. 1 is a lateral elevation view of a first embodiment of protection device;

FIG. 2 is a top view of the device of FIG. 1;

FIG. 3 is a right side view with respect to FIG. 1;

FIG. 4 is a left side view with respect to FIG. 1;

FIG. 5 is an enlarged-scale longitudinal sectional view, taken along the plane V—V of FIG. 2;

FIGS. 6 and 7 are sectional views taken along the plane VI—VI and along the plane VII—VII of FIG. 1 respectively;

FIG. 8 is a view of the device of FIGS. 1 to 7 with its half-shells in open position;

FIG. 9 is a transverse sectional view which is taken along the plane IX—IX of FIG. 1 but illustrates a variation;

FIG. 10 is a top view of a further embodiment of the protection device;

FIG. 11 is a lateral elevation view of the device of FIG. 10 with some parts in cross-section;

FIG. 12 is a left side view with respect to FIG. 11;

FIG. 13 is an enlarged-scale view of a detail of FIG. 11;

FIG. 14 is a transverse sectional view taken along the plane XIV—XIV of FIG. 13;

FIG. 15 is a partial lateral elevation view of another embodiment of the protection device;

FIG. 16 is a top view of FIG. 15;

FIG. 17 is a sectional view taken along the plane XVII—XVII of FIG. 15;

FIG. 18 is a transverse sectional view taken along the plane XVIII—XVIII of FIG. 15;

FIG. 19 is a view of the device of FIGS. 15 to 18 with its half-shells open;

FIG. 20 is a lateral elevation view of another embodiment of the protection device according to the invention;

FIG. 21 is a top view of FIG. 20;

FIG. 22 is a longitudinal sectional view taken along the plane XXII—XXII of FIG. 20;

FIG. 23 is a sectional view taken along the plane XXIII—XXIII of FIG. 21;

FIG. 24 is a lateral elevation view of another embodiment of the protection device;

FIG. 25 is a transverse sectional view, taken along the plane XXV—XXV of FIG. 24; and FIG. 26 is a partial top view of FIG. 24, with the proximal ends shown in both closed and divaricated position.

DESCRIPTION OF THE PREFERRED EMBODIMENTS

In the figures of the accompanying drawings, identical or similar parts or components have been indicated with the same reference numerals.

Initially with reference to the embodiment illustrated in FIGS. 1 to 8, the reference numeral 1 generally indicates a protection device formed by two half-shells 2 and 3 which are obtained by molding a suitable plastic material, such as polyethylene, polyvinylchloride, polypropylene, ABS, polyacrylonitrile and similar semirigid materials, and are mutually joined along a narrow longitudinal hinge band or region 4 which extends along a certain intermediate portion of the two half-shells. The region 4 acts as hinge in order to allow the half-shells 2 and 3, which are preferably manufactured by molding side by side (FIG. 8), to close onto one another, thus delimiting an internal accommodation seat with a plurality of compartments, as explained hereinafter.

On the side opposite to said intermediate portion, each half-shell is provided with a distal portion 21 and 51 and with a proximal portion 22 and 52 which have a complementarily tapered shape. Along the edge of the distal portions 21 and 51, except at the hinge band 4, there is a lip for male-female snap-coupling, for example a flange 23 with a male profile around the portion 21 and a flange 53 with an undercut female internal recess 54, so that when the two half-shells are closed and forced against one another they remain irreversibly locked and rigidly associated with one another.

The half-shell 2 has, approximately at the hinge region, an opening 24 at which it is possible to move a clamp 25, formed by a flexible wing 26 which is rigidly associated with the portion 21, is preferably made of the same material, protrudes from said portion 21 with a preset inclination and can be externally provided with a knurling 27, and by a transverse portion or guillotine portion 28 which extends transversely to the half-shell 21 starting from said wing 26 and enters the half-shell through the opening 24.

Advantageously, the guillotine portion 28 is provided, at its front face, with a lower notch 29 and an upper notch 30, both of which are provided for engagement with the tapered front edge 31 of the opening 24.

Between the edge 31 and the proximal end 22, the wall of the half-shell 2 has a thickened portion 32 which delimits, inside the half-shell, a sequence of guiding sections, i.e. a conical section 33 followed by a cylindrical section 34 which ends with a conical retention ridge 35. The taper of the proximal portion 22 starts from the section 33; said proximal portion 11 has, along its edges, at the sections 33 and 34, an indent 36 which is delimited on one side by a small lip 37 and by a protrusion 38 in the shape of an inclined plane on which said lip 37 on the half-shell 52 is intended to abut, and by a shoulder 36a on the other side.

A slightly lower portion 39 is instead provided starting from the lip 37 and the protrusion 38 toward the end of the proximal portion; said lower portion 39 is intended, together with a corresponding lower portion defined on the portion 52 of the half-shell 51, to delimit two longitudinal slits 40 which are for example approximately 1 mm high.

The half-shell 3 is internally provided with a conical cavity 54 at its distal portion, followed by an intermediate planar section 55 and by sections 33 and 34 in its intermediate portion.

If required, the proximal ends 22 and 52 of the half-shells 2 and 3 can be internally provided with an absorbing tampon 56 which is fixed, for-example glued inside them, in order to absorb possible small reflux losses (at the most a drop) from the needle 70, as will be further explained hereinafter.

The above described protection device is used as follows. The butterfly needle 70, which is connected to a flexible tube 72 for feeding infusion fluid or reinfusion or transfusion blood or for withdrawing blood, is inserted in a vein or arteriovenous fistula and fixed in position on the patient's body in the conventional manner, for example by applying a first transverse portion of adhesive tape above the proximal portion of the needle 70 and of the wings 71, a second portion of "cravat" adhesive tape which passes below the distal part of the needle and above the wings 71 to slightly raise the distal part of the needle and prevent its retraction, and a third portion of adhesive tape which is parallel to the first portion and is arranged above the first and second portions and above the wings.

When the withdrawal or infusion operation has occurred, the half-shells 2 and 3 are closed in a snap-together manner around the tube 72 before the needle is removed. If necessary, the device 1 is then caused to slide and is held with one of the operator's hands between the index and the thumb, which is pressed on the wing 26 for a safer grip, acting with the other fingers of the hand on the flexible tube 72 so as to make said tube slide in the direction of extraction from the device 1, toward the butterfly needle 70, until the wings 71 are inserted in the longitudinal slits 40. Accordingly, the proximal end 51 of the half-shell 3 partially inserts itself below the intermediate portion between the wings 71 until its proximal end reaches the region of a hemostatic tampon which is held by the operator's other hand at the needle insertion point. Simultaneously, the tip of the proximal portion 21 of the half-shell 2 arranges itself over the needle insertion point, so as to be able to act as shield against possible spraying of blood during needle removal.

The needle removal operation is started by then acting on the tube 72 with the middle, ring and little fingers of the hand which holds the device, causing the wings 71 to slide along the slits 40, so that the needle gradually enters the seat inside the device 1. As the maneuver continues, the wings 71 pass beyond the barrier constituted by the lip 37 and by the protrusion 38, also by virtue of the inclined-plane configuration of the latter, and move into the region delimited by the lower portions 36 in abutment against the shoulder 36a.

At the same time, the end of the tube 72 which is inserted on the body of the needle 70 in the internal seat of the device 1 is slightly forced so that it slides along the conical inclined-plane sections 33 so as to engage against the ridges 35 and move the guillotine 28 backward, disengaging it from the edge 31. The operator, by pressing on the clamp 25, can then squeeze the flexible tube 72 so as to choke it in order to prevent the escape of fluid or blood from the needle 70, and moves the guillotine so that it engages the edge 31 with its own upper notch 30.

In this condition, the device 1, which contains the needle 70 and the flexible tube 72 well-protected inside it, can be safely handled by the operator for its disposal.

If a drop of fluid or blood escapes from the tip of the needle 70 as a consequence of the choking action of the guillotine, said drop is immediately absorbed by one of the tampons 56 provided within the proximal portions 22 and 52. It should be noted that during the entire operation for the removal of the needle 70, the operator is never in direct contact with the needle 70 and does not risk puncturing himself, since the needle 70 is well-protected by the device. Besides, at the end of the operation, since the tube 72 is choked by the guillotine 28 there is also no risk of contaminating the environment in the vicinity of the operator or of the patient with unwanted leakages of fluid or blood.

The variation of FIG. 9 illustrates a device 1 whose distal portion is a single tubular part 61. With this variation, before use it is necessary to insert the flexible tube 72 through the distal opening 61 of the device.

FIGS. 10 to 14 relate to a protection device 80 whose distal end 81 is formed by a tubular segment which can be connected to the body 82 of the device, for example by means of a snap-coupling between a male flange 83 defined at the tapered end 84 of the body 82 and an annular undercut recess defined in an expansion 85 of the internal opening of the tubular end 81 (FIG. 13).

The distal end furthermore has two terminal lateral openings 86 which upwardly delimit a tab 87 which is provided with a wedge-like expansion 88 directed inward and downwardly delimit a closure strip 89 which ends with two fork-like arms 90 between which the flexible tube 70 can pass. The arms 90 are folded toward the tab 87 and have saw-tooth notches 91 for engaging the front of the tab 87. Said tab can be forced by a finger of the operator to move downward, squeezing the flexible tube 72, but cannot move backward so as to loosen, since it is prevented from doing so by the notches 91.

The proximal end of the device 80 is similar to the one of the device 1, and is provided with lateral longitudinal slits 40, so that the device 80 operates substantially like the device 1, with the difference that before using the butterfly needle 70 it is necessary to insert the tube 72 both within the body 82 and in the distal end 81. Once the limit of the stroke for the removal of the needle 70 has been reached, after the wings of said needle have moved into abutment against the shoulders 36a, the operator presses the tab 87, which slides along the saw-tooth notches 91, against the tube 72, which thus remains completely and permanently blocked.

FIGS. 15 to 19 illustrate a protection device 95 which is formed by two half-shells 2 and 3 which are mutually joined along a hinge region 4 at their non-tapered distal end 21 and 51. Both along their distal end and at their proximal end 22 and 52, the half-shells 2 and 3 have a male-female flange 23 and 53 for their snap-together coupling; the flange can be external to the half-shells (FIGS. 16 and 19) or internal thereto (FIGS. 17 and 18). Lowered portions 39 are provided between the flanges 23 and 53 and therefore do not extend along the entire length of the proximal portions of the half-shells, so that once they are closed onto one another, said half-shells delimit longitudinal openings 40a provided with a proximal stop abutment 39d and a distal one 36a.

At its distal end, the half-shell 2 is provided with an opening 24 in which a clamp 25 with a tab 26 and a guillotine 28, fully similar to the one of the device 1, is provided.

The device 95 must be closed around a needle 70 so that the wings 71 thereof remain engaged, but free to slide, within the openings 40a. It otherwise operates like the device 1.

The embodiment illustrated in FIGS. 20 to 23 relates to a protection device 100 which is similar to the device 1 but in which the longitudinal slits 40 are respectively defined on the half-shell 2 and on the half-shell 3, which can be closed together in a snap-together manner along their entire contour, which is offset by 90° with respect to the slits 40. One of the half-shells, for example the half-shell 2, is internally provided with a longitudinal tab 101 at its distal end 21. Said tab is weakened in an intermediate region, its distal end is rigidly associated with the wall of the half-shell 2 and its proximal end is freely movable and has a step-like expansion 103 which is suitable for engaging the front of the needle 70 during its backward movement within the device during its removal. Once the end 103 of the tab has engaged the needle, said tab is moved backward and forced to deform at its region 102, which presses into the flexible tube 72 and chokes it.

Advantageously, the protection device 100 can have outer recesses 104 for safer and more comfortable grip on the part of the operator during the operation for the removal and retraction of the needle 70.

FIGS. 24 to 26 illustrate a protection device 105 whose distal end is similar to the one of the device 80, whereas the proximal end is constituted by a tubular portion 106 ending with two half-shells 107 and 108 which are hinged at one end to the tubular portion 106, so that they can be divaricated or opened and closed against one another. For this purpose, each half-shell is connected to the tubular portion 106 by means of a pair of rod-like elements 109 and 110 which extend longitudinally with respect to the device and have one end rigidly associated with the tubular body 106 and the other end rigidly associated with the respective half-shell.

The contour edge of one of the half-shells, for example the half-shell 108, is concave or inclined inward (FIG. 25), whereas the contour edge of the half-shell 107 is complementarily, i.e. it is convex or has the same inclination as the edge of the half-shell 108. This configuration of the edges ensures, in addition to perfect closure, a guiding action which facilitates the closure of the two half-shells.

The half-shells 107 and 108 may be provided, at their tips, with means for mutual engagement and retention, such as for example a tooth 111 on one of said half shells and an undercut recess 112 on the other half-shell for mutual snap-together engagement in closed position.

Two opposite openings 40a extend partially along the tubular portion 106 and partially along a portion of each half-shell 107 and 108, and a respective wing 71 of a butterfly needle 70 can enter said openings during the closure of the half-shells 107 and 108.

The use of the device 105 is similar to the use of the device 80. Before use, it is necessary to divaricate the half-shells 107 and 108, insert the tube 72 both along the tubular portion 106 and along the distal end B1, prepare the needle at the outlet of the tubular portion 106 so that its wings engage the openings 40a at least with their distal edge, and then it is possible to insert the needle in a vein for an infusion or withdrawal operation. Once the operation is completed, the operator grips the device 105, retracts the needle 70 so that it enters the internal seat of the tubular portion 106, passing beyond the inclined plane 38, snap-closes the half-shells 107 and 108 together with the other hand, and then presses the tab 87 against the flexible tube 72. The needle 70 remains thus completely enclosed within the device 105 so as to completely protect against both accidental punctures and any oscillation.

We claim:

1. Device for protecting against accidental butterfly needle punctures comprising a hollow body which delimits an internal accommodation seat for a butterfly needle connected to a flexible duct for feeding or withdrawing fluid, said seat having a proximal terminal portion, said hollow body being provided with two longitudinal lateral slits in each of which a respective wing of the butterfly needle can slidingly engage, and a distal terminal portion provided with retention means for the engagement of the butterfly needle, so that said butterfly needle can slide along said seat from a removal start position in the proximal terminal portion toward an irreversible complete retraction position within the distal terminal portion, wherein closure means suitable for engaging and choking the flexible duct in order to prevent the escape of residual fluid or blood from the needle are provided between the proximal terminal portion and the distal terminal portion of said accommodation seat and wherein said closure means comprise an opening defined in the distal terminal portion, a transverse tube choking element which is suitable for moving through said opening, and engagement means for said choking element which are suitable for allowing the sinking of said choking element toward the inside of said internal seat but not its retraction.

2. Device according to claim 1, characterized in that said choking element comprises a flexible supporting tab which extends longitudinally with respect to said opening, said tab having a transverse portion, said transverse portion of said tab acting as a closure guillotine which can be sunk into the internal seat by pressing on said tab.

3. Device according to claim 2, wherein said transverse portion of said tab comprises a guillotine portion, and wherein said engagement means comprise a plurality of notches, said plurality of notches being defined on said guillotine portion and intended to engage an edge of the distal portion.

4. Device according to claim 1, wherein said slits are open toward the proximal terminal portion.

5. Device for protecting against accidental butterfly needle punctures comprising;
   a hollow body;
   an internal accommodation seat defined within said hollow body for accommodating a butterfly needle of the type having wings and being connected to a flexible duct;
   a proximal terminal portion defined by said seat,
   a distal terminal portion defined by said seat,
   two longitudinal lateral slits provided in said proximal terminal portion for slideably engaging wings of a butterfly needle movable from a removal start position, at said proximal terminal portion, to a retraction position at said distal terminal portion, and;
   means for irreversibly locking a butterfly needle in said retraction position and simultaneously choking a flexible duct connected to such butterfly needle.

6. Device according to claim 5, wherein said means for irreversibly locking a butterfly needle in said retraction position and simultaneously choking a flexible duct connected to such butterfly needle comprise,
   an opening formed in said hollow body;
   an externally accessible flexible wing connected to said hollow body, and;
   a transverse portion extending transversely with respect to said internal accommodation seat, said transverse portion being connected to said flexible wing and penetrating said opening.

7. Device according to claim 6, wherein said externally accessible flexible wing is inclined with respect to said hollow body.

8. Device according to claim 5, wherein said means for irreversibly locking a butterfly needle in said retraction position and simultaneously choking a flexible duct connected to such butterfly needle comprise,
   an opening formed in said hollow body;
   an externally accessible flexible wing connected to said hollow body;
   a transverse portion extending transversely with respect to said internal accommodation seat, said transverse portion being connected to said flexible wing and penetrating said opening;
   an edge defined by said hollow body at said opening and facing said transverse portion, and;
   engagement means connected to said transverse portion and engaging said edge.

9. Device according to claim 8, wherein said edge is a tapered edge, and wherein said engagement means comprise a plurality of notches, each of said notches being engageable with said tapered edge.

10. Device according to claim 8, wherein said slits lie on a plane, and wherein said transverse portion extends substantially perpendicular with respect to said slits.

11. Device according to claim 8, further comprising, in combination, a butterfly needle and a flexible duct connected to said butterfly needle, wherein said edge is a tapered edge, and wherein said engagement means comprise two notches including an upper notch and a lower notch, said lower notch being engageable with said tapered edge for maintaining said transverse portion in a position of non interference with said flexible duct, said upper notch being engageable with said tapered edge for permanently locking said transverse portion in a position choking said flexible duct and irreversibly locking said butterfly needle in said retraction position.

12. Combination according to claim 11, wherein said needle has connected thereto means for engaging said transverse portion in said retracted position of said needle, whereby to disengage said engagement means from said edge.

13. Device according to claim 5, wherein said distal terminal portion comprises a single tubular part.

14. Device according to claim 5, wherein said means for irreversibly locking a butterfly needle in said retraction position and simultaneously choking a flexible duct connected to such butterfly needle comprise;
   a closure strip connected to said hollow body;
   saw-tooth notches formed on said closure strip;
   a tab hinged to said hollow body opposite said strip and engageable with said saw-tooth notches, and
   a wedge-like expansion connected to said tab and directed inwardly towards said internal accommodation seat.

15. Device according to claim 5, wherein said hollow body comprises;
   two half shells;
   a hinge region mutually joining said half shells;
   a male flange provided on one of said half shells;
   a female flange provided on another one of said half shells and engaging said male flange;
   lowered portions provided on said male flange and on said female flange;
   longitudinal openings defined between said lowered portions;
   a proximal stop abutment defined by said longitudinal opening;
   a distal stop abutment defined by said opening opposite said proximal stop abutment.

16. Device according to claim 5, wherein said means for irreversibly locking a butterfly needle in said retraction position and simultaneously choking a flexible duct connected to such butterfly needle comprise;
   a deformable tab located in said internal accommodation seat;
   a tab distal end defined by said tab and connected to said hollow body;
   a tab proximal end defined by said tab and movable within said internal accommodation seat;
   means for engaging a butterfly needle connected to said tab proximal end, and;
   a weakened and deformable intermediate tube-choking region defined between said tab distal end and said tab proximal end.

17. Device according to claim 5, wherein said hollow body comprises two half shells, and, means for mutual snap-together engagement of said half shells, one of said two longitudinal lateral slits being provided on each of said half shells and spaced from said means for mutual snap-together engagement of said half shells.

18. Device according to claim 5, wherein said hollow body comprises;
   a tubular proximal portion;
   two half shells each having an end, said end of each of said half shells being hinged to said tubular proximal portion;
   tips defined by said half shells remote from said tubular proximal portion, and;
   means for engaging and retaining together said tips of said half shells;
   said two longitudinal lateral slits extending along said two half shells and partially along said tubular proximal portion.

19. In combination, a device for protecting against accidental butterfly needle punctures, a butterfly needle having wings, and a flexible duct connected to said butterfly needle, said device comprising;
   a hollow body;
   an internal accommodation seat defined within said hollow body for accommodating said butterfly needle;
   a proximal terminal portion defined by said seat,
   a distal terminal portion defined by said seat;
   two longitudinal lateral slits provided in said proximal terminal portion for slideably engaging said wings of said butterfly needle, said butterfly needle being movable from a removal start position, at said proximal terminal portion, to a retraction position at said distal terminal portion, and;
   means for irreversibly locking said butterfly needle in said retraction position and simultaneously choking said flexible duct,
   wherein said means for irreversibly locking said butterfly needle in said retraction position and simultaneously choking said flexible duct comprise,
   an opening formed in said hollow body;
   an externally accessible flexible wing connected to said hollow body, and;
   a transverse portion extending transversely with respect to said internal accommodation seat, said transverse portion being connected to said flexible wing and penetrating said opening.

20. Combination according to claim 19, wherein said externally accessible flexible wing is inclined with respect to said hollow body.

21. Combination according to claim 19, wherein said means for irreversibly locking said butterfly needle in said retraction position and simultaneously choking said flexible duct comprise,
   an opening formed in said hollow body;
   an externally accessible flexible wing connected to said hollow body;
   a transverse portion extending transversely with respect to said internal accommodation seat, said transverse portion being connected to said flexible wing and penetrating said opening;
   an edge defined by said hollow body at said opening and facing said transverse portion, and;
   engagement means connected to said transverse portion and engaging said edge.

22. Combination according to claim 21, wherein said edge is a tapered edge, and wherein said engagement means comprise a plurality of notches, each of said notches being engageable with said tapered edge.

23. Combination according to claim 21, wherein said transverse portion extends substantially perpendicular with respect to said slits and said butterfly needle.

24. Combination according to claim 21, wherein said edge is a tapered edge, and wherein said engagement means comprise two notches including an upper notch and a lower notch, said lower notch being engageable with said tapered edge for maintaining said transverse portion in a position of non interference with said flexible duct, said upper notch being engageable with said tapered edge for permanently locking said transverse portion in a position choking said flexible duct and irreversibly locking said butterfly needle in said retraction position.

25. Combination according to claim 21, wherein said hollow body comprises;
   two half shells;
   an intermediate portion defined by each of said half shells;
   a hinge region interconnecting each said intermediate portion;
   a half shell distal portion defined by each of said half shells;
   a half shall proximal portion defined by each of said half shells;
   a profiled flange formed on each said half shell distal portion, and;
   an internally recessed flange formed on each said half shell proximal portion;
   wherein said profiled flange engage said internally recessed flange for irreversibly locking said two half shells together, and,
   wherein said needle has connected thereto means for engaging said transverse portion in said retracted position of said needle.

* * * * *